US00PP21972P2

(12) United States Plant Patent
Woolmore

(10) Patent No.: US PP21,972 P2
(45) Date of Patent: Jun. 7, 2011

(54) ***UNCINIA* PLANT NAMED 'BELINDA'S FIND'**

(50) Latin Name: *Uncinia rubra*
Varietal Denomination: Belinda's Find

(76) Inventor: Malcolm Woolmore, Auckland (NZ)

( * ) Notice: Subject to any disclaimer, the term of this patent is extended or adjusted under 35 U.S.C. 154(b) by 0 days.

(21) Appl. No.: 12/589,705

(22) Filed: Oct. 26, 2009

(51) Int. Cl.
*A01H 5/00* (2006.01)

(52) U.S. Cl. ..... Plt./384

(58) Field of Classification Search ..... Plt./384
See application file for complete search history.

(56) References Cited

OTHER PUBLICATIONS

GTITM UPOVROM Citation for 'Belinda's Find' as per QZ PBR 20081767; Aug. 18, 2008.*

* cited by examiner

*Primary Examiner* — Kent L Bell

(57) ABSTRACT

A new and distinct cultivar of *Uncinia* plant named 'BELINDA'S FIND' that is characterized by compact clumping habit and bronze-green leaves each with bright cherry-red margins. In combination these traits set 'BELINDA'S FIND' apart from all other existing varieties of *Uncinia* known to the inventor.

1 Drawing Sheet

Genus: *UNCINIA*.
Species: *rubra*.
Denomination: 'BELINDA'S FIND'.

BACKGROUND OF THE INVENTION

The present invention relates to a new and distinct cultivar of *UNCINIA* which is an ornamental sedge grown for use in the garden and landscape. The new invention is classified in the family Cyperaceae and is known botanically as *UNCINIA rubra* and will be referred to hereinafter by the cultivar name 'BELINDA'S FIND'.

'BELINDA'S FIND' was discovered by the inventor as a naturally occurring branch sport derived from the parent an individual *Uncinia rubra* (unpatented). The inventor discovered 'BELINDA'S FIND' in January 2002 in a commercially grown crop of *Uncinia rubra* (species, unpatented) at the inventor's nursery in Auckland, New Zealand. Selection was based on the criterion of foliage color. The closest comparison plant is the species parent. Whereas the species parent exhibits uniformly bronze-green foliage, the foliage of 'BELINDA'S FIND' bears distinct and prominent bright cherry-red margins.

'BELINDA'S FIND' exhibits compact clumping habit, and bronze-green leaves, each with bright cherry-red margins that illuminate the foliage. 'BELINDA'S FIND' is ideal for use in perennial borders, or as a container plant to brighten autumn and winter landscapes on patio or terrace. Dimensions the first year are 0.20 meter in height and width. Dimensions at maturity are 0.25 meter in height and width. Asexual propagation is accomplished through the methods of division and tissue culture. Cultural requirements include free-draining soil, full to partial shade, and moderate to regular water. 'BELINDA'S FIND' is hardy in USDA Zones 8-11.

The first asexual propagation of 'BELINDA'S FIND' was conducted by the inventor in Auckland, New Zealand. Asexual propagation was accomplished at the inventor's nursery in September 2002. The method of reproduction used was division. Since that time under careful observation 'BELINDA'S FIND' has been determined fixed, stable, uniform, and to reproduce true to type in successive generations of asexual propagation.

SUMMARY OF THE INVENTION

The following traits have been repeatedly observed and represent the distinguishing characteristics of 'BELINDA'S FIND'. These traits in combination set 'BELINDA'S FIND' apart from all other existing varieties of *Uncinia* known to the inventor. 'BELINDA'S FIND' has not been tested under all possible conditions and phenotypic differences may be observed with variations in environmental, climatic, and cultural conditions without however any variance in genotype.

1. 'BELINDA'S FIND' exhibits compact clumping habit.
2. 'BELINDA'S FIND' exhibits bronze-green leaves, each with bright cherry-red margins that illuminate the foliage.
3. 'BELINDA'S FIND' is asexually propagated by the methods of division and tissue culture.
4. 'BELINDA'S FIND' is 0.20 meter in height and width the first year, and 0.25 meter in height and width at maturity.
5. 'BELINDA'S FIND' is hardy in USDA Zones 8-11.

BRIEF DESCRIPTION OF THE DRAWING

The accompanying color drawing illustrates the overall appearance of 'BELINDA'S FIND' showing the color as true as is reasonably possible to obtain in color reproductions of this type. Color in the drawing may differ from color values cited in the detailed botanical description, which accurately describe the actual color of 'BELINDA'S FIND'. The plant exhibited in the drawing is 3-years-old and growing out-of-doors in partial shade. Drawing labeled

BOTANICAL DESCRIPTION OF THE PLANT

Figure 1:
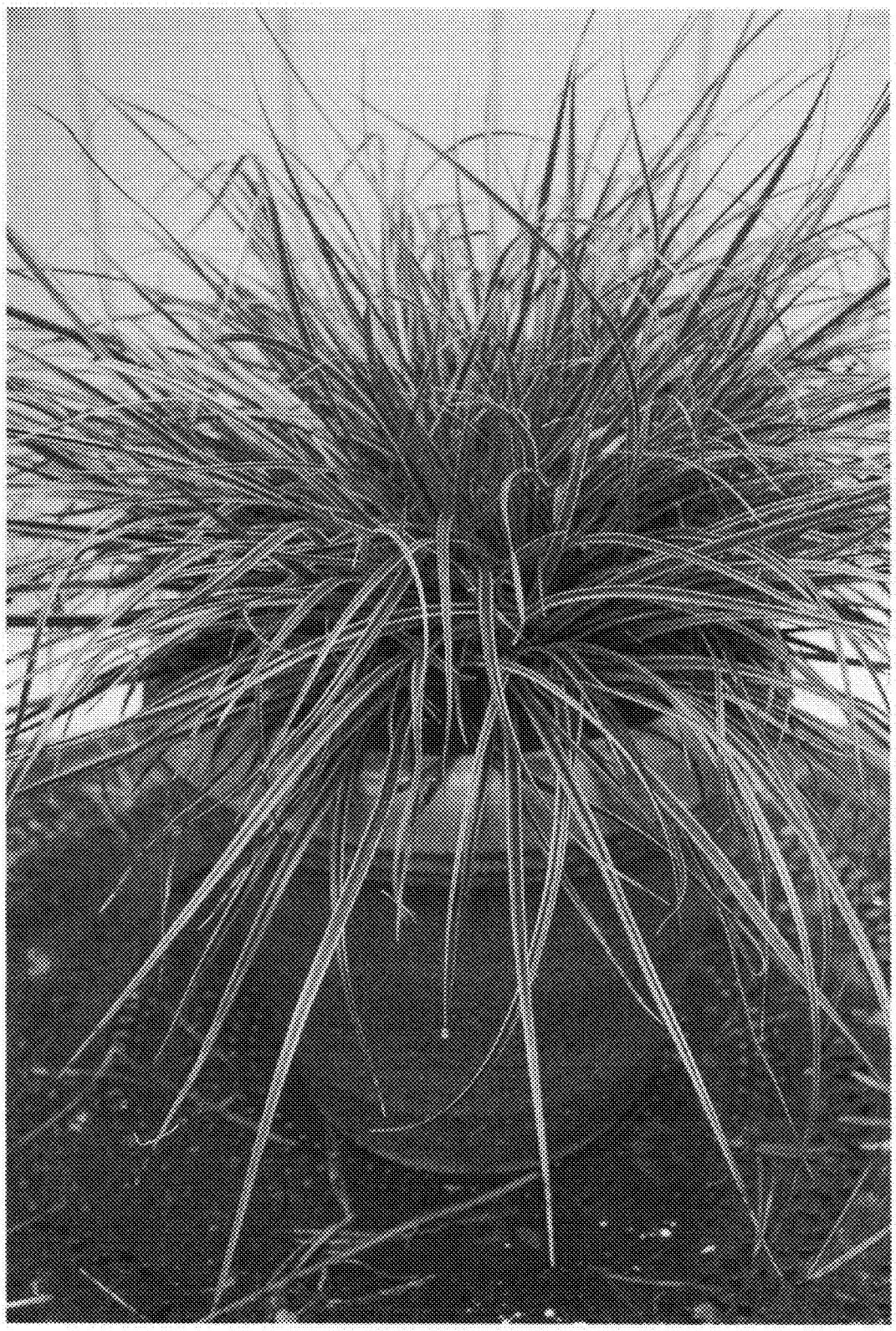
FIG. 1 illustrates the habit and foliage color of 'BELINDA'S FIND'. The drawing was made using conventional techniques and although foliage may appear different from actual color due to light reflectance, color is as accurate as possible by conventional photography.

The following is a detailed botanical description of 'BELINDA'S FIND'. Observations, measurements, values and comparisons were collected in the month of January 2009 in Arroyo Grande, Calif., from 3-year-old plants growing in the ground, that were transplanted from 1-liter container plants. Color determinations are made in accordance with The 2001 Royal Horticultural Society Colour Chart from London, England, except where general color terms of ordinary dictionary significance are used. The growing requirements of 'BELINDA'S FIND' are similar to the species.

Botanical classification: *UNCINIA rubra* 'BELINDA'S FIND'.
Family: Cyperaceae.
Genus: *UNCINIA*.
Species: *rubra*.
Denomination: 'BELINDA'S FIND'.
Common name: Belinda's sedge.
Habit: Compact clumping.
Plant shape: Fountain-shaped.
Commercial category: Tufted herb.
Use: Perennial border or container plant for patio or terrace.
Suggested commercial container size: 1-liter container.
Parentage: *UNCINIA rubra* 'BELINDA'S FIND' was discovered as a naturally occurring branch sport derived from the following:
*Parent.*—An individual *Uncinia rubra* (unpatented).
Propagation method: Division and tissue culture.
Rooting system: Fibrous.
Vigor: Moderate.
Crop time (range): 9-12 months to produce a 1-liter container from division.
Temperature (range): The recommended air temperature is 20-21° Centigrade.
Dimensions first year (average): 0.20 meter in height and width.
Dimensions at maturity (average): 0.25 meter in height and width.
Cultural requirements: Grow in freely draining soil and full shade to partial shade, with moderate to regular water.
Pest or disease resistance: None known to the inventor.
Pest or disease susceptibility: Typical to the species.
Hardiness: USDA Zones 8-11.
Foliage:
*Type.*—Evergreen.
*Leaf arrangement.*—Basal.
*Leaf quantity* (*average*).—>500 per individual plant.
*Leaf division.*—Simple.
*Leaf margin.*—Scabrous.
*Leaf appearance* (*abaxial and adaxial surfaces*).—Semi-glossy.
*Attachment.*—Basal sheath.
*Leaf shape.*—Linear.
*Blade length* (*range*).—22-31 cm.
*Blade width* (*average*).—0.40 cm.
*Leaf blade color* (*abaxial surface*).—200A, 147A and 179A.
*Leaf blade color* (*adaxial surface*).—200A, 147A and 179A.
*Blade surface* (*abaxial*).—Punctate.
*Blade surface* (*adaxial*).—Glabrous.
*Sheath length* (*average*).—2.5 cm.
*Sheath width* (*average*).—0.40 cm.
*Sheath appearance.*—Glossy.
*Sheath color* (*abaxial surface*).—199D.
*Sheath color* (*adaxial surface*).—199D.
*Sheath surface.*—Glabrous.
*Leaf apex.*—Cirrhose.
*Leaf base.*—Truncate.
*Venation pattern.*—Parallel.
*Vein color* (*abaxial and adaxial surfaces*).—147B.
*Leaf fragrance.*—None observed.
Inflorescence:
*Type.*—Simple spike.
*Dimensions* (*average*).—6 cm long and 5 mm. in width.
*Color* (*range*).—199A to 199D.
*Aspect.*—Erect.
*Blooming season.*—Summer.
*Quantity* (*range*).—25-70.
*Culm.*—Quantity (range): 25-70. Length (average): 35 cm. Width (average): 1 mm. Shape: Trigonous tapering toward tip. Strength (range): Rigid to wiry. Surface: Minutely scabrous on angles. Color: 146A. Leaves: 2-5 per culm. Internode (range): 3-10 mm.
*Flower.*—Type: Androgynous. True perianth: Absent. Staminate flower: Terminal portion of spike. Staminate flower length: 3 mm. Staminate flower width: 6 mm. Staminate flower color: 161A. Stamens: 3 in number protruding from spike. Pistillate flower quantity (range): 6-13. Styles: 3 in number. Pistillate flower form: Enclosed in utricle. Utricle open or closed: Closed. Utricle shape (range): Fusiform to convex. Utricle length (range): 5.0 to 6.5 mm. Utricle diameter. 1 mm. Utricle color (range): Yellow-green 152A fading to yellow-brown N167A. Utricle surface: Striate. Stipe length (range): 1.0 to 1.5 mm. Rachilla: Rachilla length: 9 mm. Rachilla diameter: <0.50 mm. Rachilla shape: Trigonomous. Rachilla Texture: Wiry. Rachilla color: Red/brown, N186C. Rachilla position: Beyond mouth of utricle terminating in a glume. Glume shape: Sharply reflexed hook. Glume dimensions (range): 2-6 mm. Glume apex: Subacute. Glume margin: Entire. Glume color (abaxial surface): 152A fading to N167A. Glume color (adaxial surface): 152A fading to N167A. Glume length (average). 5 mm. Glume width (average): 2 mm. Surface texture: Coriaceous.
*Persistent or self-cleaning.*—Persistent.

The invention claimed is:

1. A new and distinct cultivar of *Uncinia* plant named 'BELINDA'S FIND' as described and illustrated herein.

* * * * *